United States Patent
Mumme

[11] Patent Number: 6,086,614
[45] Date of Patent: Jul. 11, 2000

[54] ORTHOPEDIC PROSTHESIS HAVING ANTI-BACKOUT SCREW

[75] Inventor: Charles W. Mumme, Austin, Tex.

[73] Assignee: Sulzer Orthopedics Inc., Austin, Tex.

[21] Appl. No.: 09/012,500

[22] Filed: Jan. 23, 1998

[51] Int. Cl.[7] .................. A61F 2/38; A61F 2/30
[52] U.S. Cl. .................................. 623/20; 623/18
[58] Field of Search ............ 623/20, 18; 128/92

[56] References Cited

U.S. PATENT DOCUMENTS

| | | | |
|---|---|---|---|
| 4,640,271 | 2/1987 | Lower | 128/92 |
| 4,672,979 | 6/1987 | Pohndorf | 128/784 |
| 5,683,472 | 11/1997 | O'Neil et al. | 623/20 |
| 5,766,255 | 6/1998 | Slamin et al. | 623/20 |
| 5,879,389 | 3/1999 | Koshino | 623/20 |

Primary Examiner—Michael J. Milano
Assistant Examiner—Hieu Phan
Attorney, Agent, or Firm—Philip S. Lyren; Kenneth S. Barrow

[57] ABSTRACT

An implantable orthopedic prosthesis includes a screw having a threaded shank and a head. The head includes a plurality of splines extending outwardly of the diametrical extent of the head. A first implantable prosthetic element has a threaded bore for receiving the threaded shank of the screw in threaded engagement. A second implantable prosthetic element has a shoulder-stepped bore for receiving the threaded shank therethrough and for engaging the head. The bore includes an annular groove for receiving the splines of the head and defines a shoulder for engaging the splines to prevent backout of the screw.

3 Claims, 3 Drawing Sheets

ORTHOPEDIC PROSTHESIS HAVING ANTI-BACKOUT SCREW

BACKGROUND OF THE INVENTION

1. Field of the Invention

The present invention relates generally to implantable prostheses for replacing human skeletal joints, and relates more particularly to an anti-backout screw for use with an implantable prosthesis.

2. Background Art

Implantable orthopedic prostheses, in one form, comprise manufactured replacements for the ends and articulating surfaces of the bones of the skeleton. Such prostheses are implanted to repair or reconstruct all or part of an articulating skeletal joint that is functioning abnormally due to disease, trauma, or congenital defect. Among the various articulating skeletal joints of the human body that are eligible to be fitted with implantable orthopedic prostheses, the knee joint is often treated with such prostheses. The knee joint is a major weight bearing joint and degenerates more quickly than some other joints in case of abnormality. Also, the knee joint plays a critical role in ambulation and quality of life, resulting in great demand for surgical correction of abnormalities.

The human knee joint involves three bones: the femur, the tibia and the patella, each having smooth articulation surfaces arranged for articulation on an adjacent articulation surface of at least one other bone. The femur includes at its distal extremity an articulation surface having medial and lateral convex condyles separated posteriorly by an intercondylar groove running generally in the anterior-posterior direction. The condyles join at the distal-anterior face of the femur to form a patellar surface having a shallow vertical groove as an extension of the intercondylar groove. The patella includes on its posterior face an articulation surface having a vertical ridge separating medial and lateral convex facets, which facets articulate against the patellar surface of the femur and against the medial and lateral condyles during flexion of the knee joint, while the vertical ridge rides within the intercondylar groove to prevent lateral displacement of the patella during flexion. The tibia includes at its proximal end an articulation surface having medial and lateral meniscal condyles that articulate against the medial and lateral condyles, respectively, of the femur. The mutually engaging articulation surfaces of the femur and the patella together form, functionally, the patellofemoral joint, and the mutually engaging articulation surfaces of the femur and tibia together form, functionally, the tibiofemoral joint, which two functional joints together form the anatomical knee joint.

One or more of the articulation surfaces of the knee joint may fail to act properly, requiring the defective natural articulation surface to be replaced with a prosthetic articulation surface provided by an implantable prosthesis. To fit defects of varying scope, while allowing healthy portions of the knee joint to be conserved, a range of types of orthopedic knee implants is available. The range extends from total knee prosthesis systems for replacing the entire articulation surface of each of the femur, tibia and patella, to simpler systems for replacing only the tibiofemoral joint, or only one side (medial or lateral) of the tibiofemoral joint, or only the patellofemoral joint. Commonly employed orthopedic knee prostheses include components that fall within one of three principle categories: femoral components, tibial components, and patellar components. A so-called "total" knee prosthesis includes components from each of these categories. The femoral component replaces the distal end and condylar articulating surfaces of the femur and may include a proximal stem received within the medullary canal at the distal end of the femur. The tibial component replaces the proximal end and meniscal articulating surfaces of the tibia and may include a distal stem received within the medullary canal at the proximal end of the tibia. In some designs, the proximal stem of the femoral component or the distal stem of the tibial component is optional and is provided as a modular component. The connection between the femoral or tibial component and the respective proximal or distal stem is often accomplished via friction locking male and female conical tapered surfaces on the respective elements, also known as a Morse taper connection. Sometimes, the locking taper connection is further secured by a threaded screw extending through one element and threadedly received in the other element. The patellar component replaces the posterior side and natural articulating surface of the patella. Sometimes, the patellar component is not used, and the natural articulating surface of the patella is allowed to articulate against the femoral component.

Where a locking taper connection is employed in an implantable prosthesis, such as between a femoral or tibial component and a respective medullary stem, and further secured by a retaining screw, it is desirable that the screw be secured against backing out of the threaded bore in which it resides. Under the strain of load, the retaining screw could become loose in its threads and begin to back out, or unscrew. If the screw were to back out too far, the head of the screw could interfere with the articulating surfaces of the prosthetic joint. To avoid such an occurrence, a locking means is often employed to prevent the screw from backing out. Typically, the locking means comprises a fourth element, inserted after the screw is tightened, to cover the head of the screw and restrain the screw in its appointed location.

Using a fourth element to retain the screw has certain disadvantages: an additional step is required to insert the fourth element, thereby prolonging the implantation surgery; and the fourth element is usually small and prone to being dropped or lost during surgery. It would be desirable to provide a retaining screw, with anti-backout characteristics, that overcomes these disadvantages.

SUMMARY OF THE INVENTION

In accordance with one aspect of the invention, an implantable orthopedic prosthesis includes a screw having a threaded shank and a head. The head includes a plurality of splines extending outwardly of the diametrical extent of the head. A first implantable prosthetic element has a threaded bore for receiving the threaded shank of the screw in threaded engagement. A second implantable prosthetic element has a shoulder-stepped bore for receiving the threaded shank therethrough and for engaging the head. The bore includes an annular groove for receiving the splines of the head and defines a shoulder for engaging the splines to prevent backout of the screw.

It is an object of the present invention to provide an implantable orthopedic prosthesis having an anti-backout screw.

Other objects and advantages will be apparent from the following descriptions of a preferred embodiment.

DETAILED DESCRIPTION OF THE PREFERRED EMBODIMENT

Figure 1:
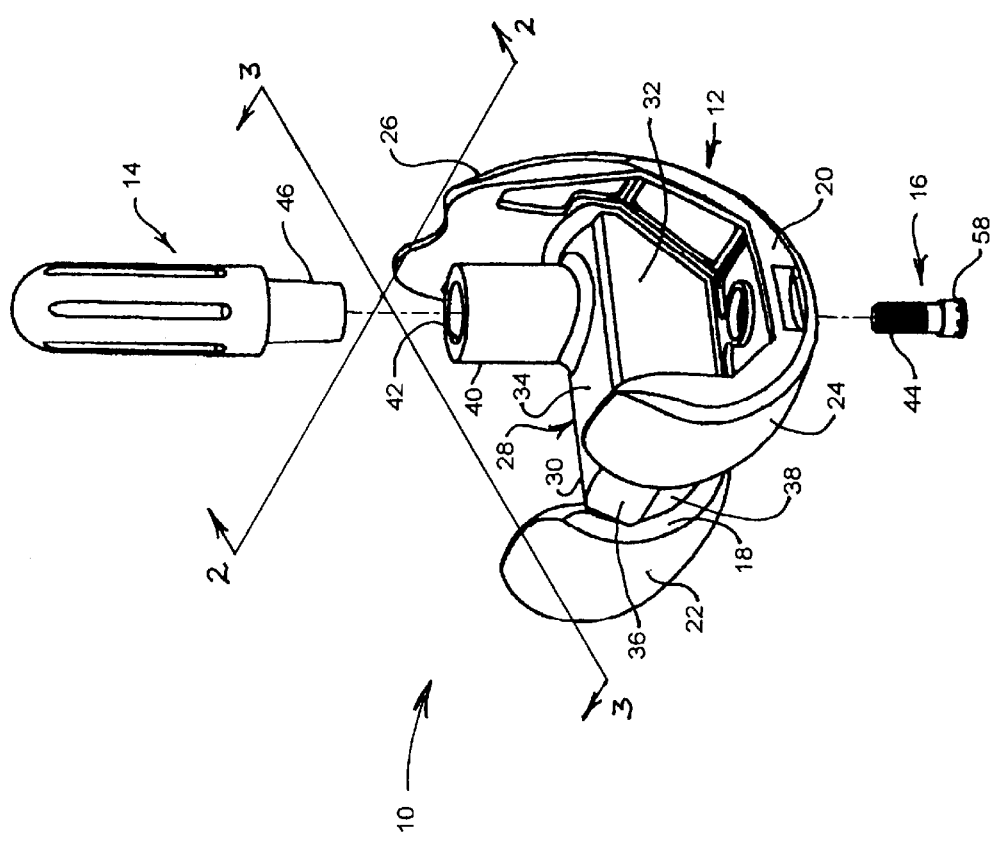
FIG. 1 is an exploded perspective view of a femoral component of an implantable knee joint prosthesis, including a modular medullary stem and a retaining screw, according to the present invention.

Referring to FIG. 1, there is illustrated a femoral component 10 of an implantable orthopedic knee joint prosthesis. Femoral component 10 includes a femoral element 12, a proximal medullary stem 14, and a retaining screw 16. Femoral element 12 is configured as a posterior stabilized, constrained condylar femoral prosthesis for use with a tibial component having a relatively high central spur that fits closely in the medial-lateral direction between the condyles of the femoral prosthesis. The configuration shown is merely illustrative, and other femoral prosthesis configurations can be employed with the present invention. Femoral element 12 includes condyles 18 and 20, having respective articulating surfaces 22 and 24. Condyles 18 and 20 are separated at the posterior and inferior aspects of femoral element 12, but are joined at the anterior aspect to form a patellar articulating surface 26. The intercondylar opening between condyles 18 and 20 is covered by a box 28 defined by side walls 30 and 32 rising from the inward edges of condyles 18 and 20, respectively, and a top wall 34. A posterior wall 36 completes box 28 and terminates in a cam follower 38 that engages the spur of the tibial component (not shown) to provide posterior stabilization. Extending superiorly from top wall 34 of box 28 is a boss 40 having a passage 42 therethrough for receiving a shank 44 of screw 16 from below, and for receiving a male taper 46 of proximal stem 14 from above.

Figure 3:
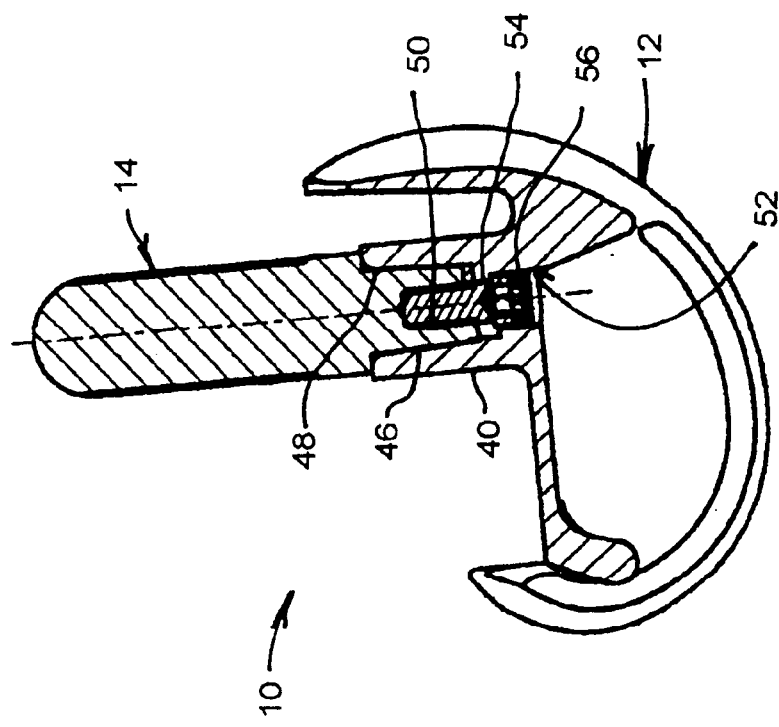
FIG. 3 is a sectional view of the femoral component of FIG. 1, taken along section plane 3—3 of FIG. 1 and viewed in the direction of the arrows.
Figure 2:
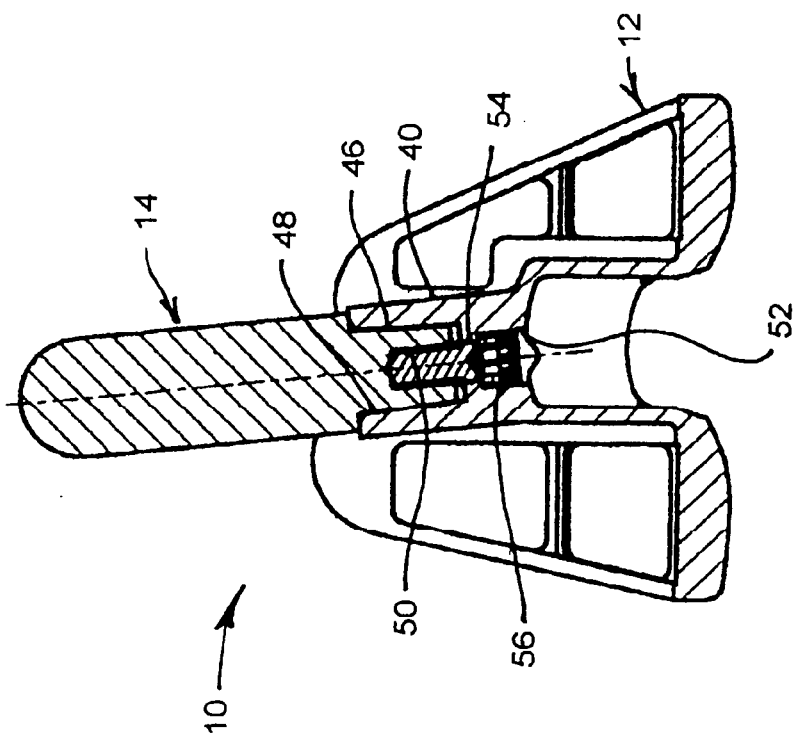
FIG. 2 is a sectional view of the femoral component of FIG. 1, taken along section plane 2—2 of FIG. 1 and viewed in the direction of the arrows.

Referring to FIGS. 2 and 3, femoral component 10 is shown assembled, in cross-section. Male conical taper surface 46 of proximal stem 14 is received in conical taper locking engagement with female conical taper surface 48 of boss 40. Threaded shank 44 of screw 16 is threadedly received in a correspondingly threaded blind bore 50 of stem 14. A shoulder-stepped bore 52 in boss 40 receives screw 16, and includes a superior portion 54 sized for free passage of shank 44 therethrough, and an inferior portion 56 sized larger than portion 54 to form an annular shoulder against which the head 58 of screw 16 bears. As screw 16 is threaded into bore 50 of stem 14, head 58 bears against the shoulder of bore 52 to draw male conical taper 46 of stem 14 into taper locked engagement with female conical taper 48.

Figure 4:
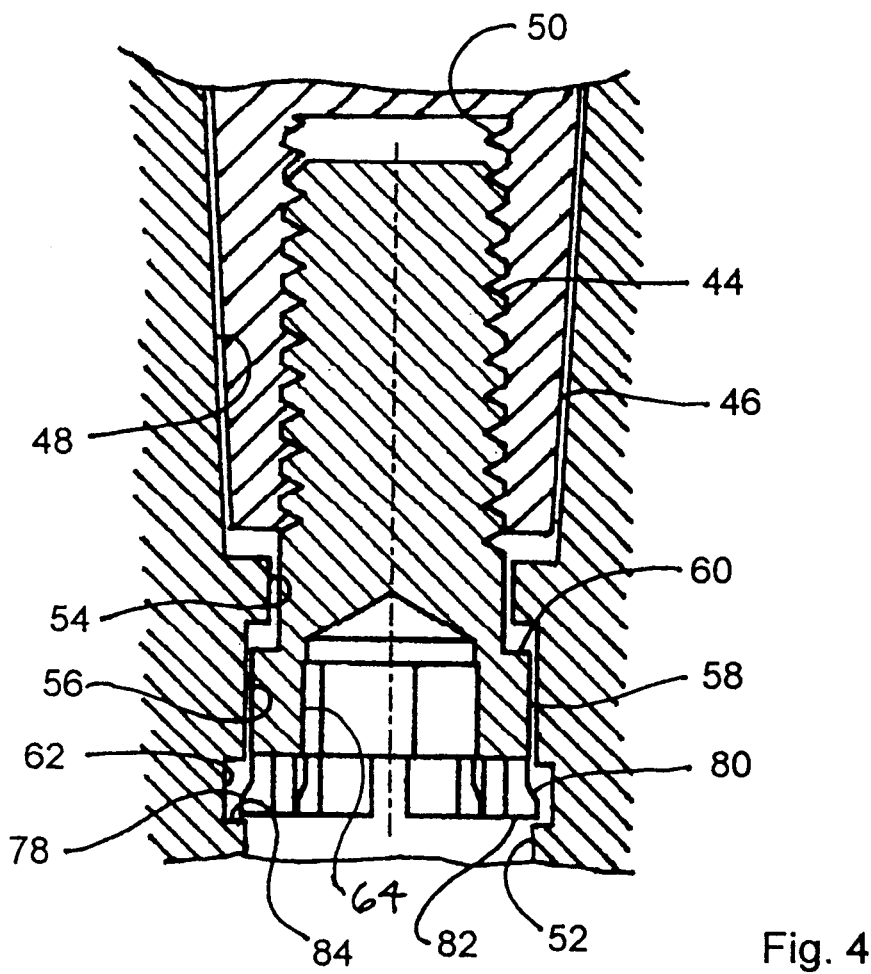
FIG. 4 is an enlarged portion of the sectional view of FIG. 2, particularly showing the retaining screw in relation to the femoral component and modular stem.
Figure 5:
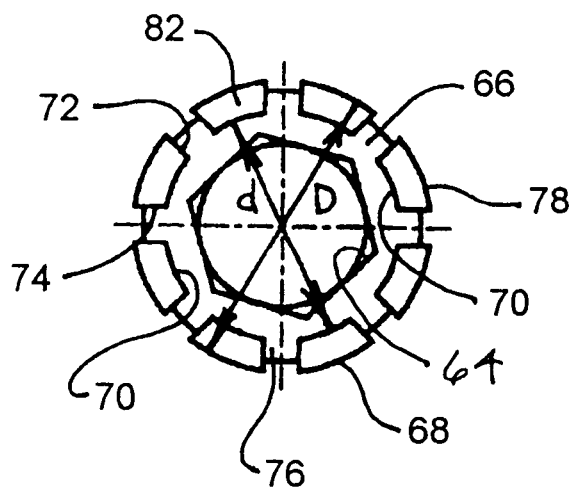
FIG. 5 is an end view of the head of the retaining screw of FIG. 4.

Referring to FIGS. 4 and 5, an enlarged cross-section of screw 16 and adjacent structures of stem 14 and femoral element 12 is shown, illustrating the anti-backout feature of the present invention. Bore 52, including superior portion 54 and inferior portion 56, discussed above, are shown clearly, as is the aforementioned annular shoulder, indicated by reference numeral 60. Likewise, male taper 46, female taper 48 and bore 50, discussed above, are shown. Bore 52 also includes an annular groove 62 therein having a maximum diameter slightly greater than that of portion 56 of bore 52. Annular groove 62, in cooperation with a portion of the head 58 of screw 16, described further below, provides the anti-backout feature of the present invention.

Again referring to FIGS. 4 and 5, head 58 of screw 16 includes a female axial recess 64 that is hexagonal in cross-section. Recess 64 is convenient for receiving a hexagonal driving tool for imparting torque to screw 16. Other polygonal cross-sections could be substituted for the hexagonal cross-section of recess 64, as desired. Head 58 includes a generally annular end-face 66 surrounding recess 64. A plurality of splines 68 extend generally axially from end-face 66, and are disposed circumferentially about end-face 66. Each of splines 68 is defined in part by an inner wall 70 lying on a common circle centered on the axis of screw 16 and having a diameter d that is less than the diameter of head 58. Each spline 68 is further defined by a pair of side walls 72 and 74, each of which lies parallel to, but offset from, a radius of screw 16. Consequently, side walls 72 and 74 of any particular spline 68 converge in a radially inward direction, whereas splines 72 and 74, respectively, of adjacent splines 68 are parallel. As preferred, an even number of splines is provided, equally spaced circumferentially, such that diametrically aligned spaces 76 are defined between adjacent splines. Each spline 68 is further defined by an outer wall 78 lying on a common circle centered on the axis of screw 16 and having a diameter D that is greater than the diameter of head 58. An interrupted frusto-conical surface 80 provides a ramped transition between head 58 and outer wall 78.

The splines 68 of screw 16, imparting a castellated appearance to the axial end of head 58, are integral with head 58 and cantilevered therefrom. Each spline 68 is capable of slight elastic deflection in the radially inward direction. As screw 16 is inserted and tightened into threaded engagement with bore 50 of stem 14, the frusto-conical surface 80 of each spline 68 is drawn into engagement with the opening of bore 52. In a caming action, each spline 68 is deflected radially inwardly until outer wall 78 is disposed at the same radial location as bore 52, whereupon outer wall 78 engages bore 52 in spring tension as screw 16 advances. As soon as the axial ends 82 of the splines 68 reach annular groove 62 of bore 52, splines 68 rebound elastically radially outwardly such that outer wall 70 is disposed within groove 62 and ends 82 of splines 68 are retained against backout by shoulder 84 of groove 62.

The present invention has been illustrated and described with particularity in terms of a preferred embodiment. Nevertheless, it should be understood that no limitation of the scope of the invention is intended. The scope of the invention is defined by the claims appended hereto. It should also be understood that variations of the particular embodiments described herein incorporating the principles of the present invention will occur to those of ordinary skill in the art and yet be within the scope of the appended claims.

I claim:

1. An implantable orthopedic prosthesis comprising:

a screw having a longitudinal axis, a threaded shank, and a head with an end surface and a plurality of splines, wherein said splines extend upwardly along said longitudinal axis in a first position and have a first end that is rigidly connected to said end surface and an elastic second end that deflects in a radial direction toward said longitudinal axis;

a first implantable prosthetic element having a threaded bore for receiving said threaded shank of said screw in threaded engagement;

a second implantable prosthetic element having a shoulder-stepped bore for receiving said threaded shank therethrough and for engaging said head, said shoulder-stepped bore adapted to deflect the splines in a radial direction away from the first position, the shoulder-stepped bore including an annular groove for receiving said splines of said head and defining a shoulder for engaging said splines to prevent backout of said screw, the splines returning to the first position in the annular groove.

2. The implantable orthopedic prosthesis of claim 1, in which said splines include a frusto-conical surface at said second end; and said annular groove receives said frusto-conical surface.

3. The implantable orthopedic prosthesis of claim 2, in which said splines include an outer wall; and said frusto-conical surface extends from said outer wall and away from said longitudinal axis.

* * * * *